(12) United States Patent
Böttcher et al.

(10) Patent No.: US 6,310,068 B1
(45) Date of Patent: Oct. 30, 2001

(54) BENZONITRILES AND BENZOFLUORIDES

(75) Inventors: Henning Böttcher, Darmstadt; Karl Ulrich Bühring, Grafing; Hartmut Greiner; Gerd Bartoszyk, both of Weiterstadt; Christoph Seyfried, Seeheim-Jugenheim, all of (DE)

(73) Assignee: Merck Patent Gesellschaft mit Beschrankter Haftung, Darmstadt (DE)

( * ) Notice: Subject to any disclaimer, the term of this patent is extended or adjusted under 35 U.S.C. 154(b) by 786 days.

(21) Appl. No.: 08/628,250

(22) Filed: Apr. 5, 1996

(30) Foreign Application Priority Data

Apr. 5, 1995 (DE) ................................ 195 12 639

(51) Int. Cl.$^7$ ...................... A61K 31/496; C07D 403/06
(52) U.S. Cl. ...................... 514/254.09; 544/373
(58) Field of Search ............................ 544/373; 514/253, 514/254.09

(56) References Cited

U.S. PATENT DOCUMENTS 5,418,237 * 5/1995 Böttcher et al. ..................... 514/253

FOREIGN PATENT DOCUMENTS

| 771285 | 10/1971 | (BE) . |
|---|---|---|
| 4101686 * | 7/1992 | (DE) . |
| 376607 | 12/1989 | (EP) . |
| 496222 | 10/1992 | (EP) . |
| 1551082 | 10/1967 | (FR) . |
| 1075156 | 7/1967 | (GB) . |

* cited by examiner

*Primary Examiner*—Emily Bernhardt
(74) *Attorney, Agent, or Firm*—Millen White Zelano Branigan, P.C.

(57) ABSTRACT

Compound of the formula I

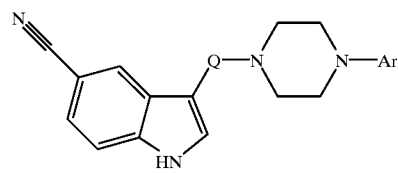

in which Q and Ar have the meanings indicated herein, and their salts, exhibit actions on the central nervous system.

17 Claims, No Drawings

BENZONITRILES AND BENZOFLUORIDES

The invention relates to compounds of the formula I

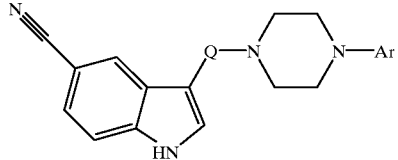

in which
- Ar is a phenyl radical which is mono- or disubstituted by CN and/or F,
- Q is $C_nH_{2n}$ and
- n is 3 or 4 and their salts, 3-[4-(4-(4-fluorophenyl)-1-piperazinyl) butyl]-5-cyanoindole and 3-[4-(4-(2-fluorophenyl)-1-piperazinyl)-butyl]-5-cyanoindole, with the exception of their salts, being excluded.

BACKGROUND OF THE INVENTION

Similar compounds have been disclosed in EP 0 376 607, BE 771285, GB 1 075 156, FR 1,551,082 and in particular in DE 41 01 686 A1 (corresponding to EP 0496 222 A1).

As regards the last-mentioned patent application, the compounds according to the invention are distinguished in comparison to the known compounds substituted by methoxy groups by an improved oral bioavailability. They are considered as a selection invention, expecially with respect to DE 41 01 686.

SUMMARY OF THE INVENTION

The invention was based on the object of finding novel compounds having useful properties, in particular those which can be used for the production of medicaments. Upon further study of the specification and appended claims, further objects and advantages of this invention will become apparent to those skilled in the art. It was found that the compounds of the formula I and their physiologically acceptable acid addition salts have very useful pharmacological properties together with good tolerability. Thus they show, in particular, actions on the central nervous system, especially 5-$HT_{1A}$-agonistic and 5-HT-reuptake-inhibiting actions. They inhibit the binding of tritiated serotonin ligands to hippocampal receptors (Cossery et al., European J. Pharmacol. 140 (1987), 143–155). In addition, changes in DOPA accumulation in the striatum and 5-HTP accumulation in N. raphe occur (Seyfried et al., European J. Pharmacol. 160 (1989), 31–41). Furthermore, analgesic and hypotensive actions occur; thus in conscious, spontaneously hypertensive rats bearing catheters (SHR strain/Okamoto/NIH-MO-CHB-Kisslegg; method cf. Weeks and Jones, Proc. Soc. Exptl. Biol. Med. 104 (1960), 646–648) the blood pressure measured directly after oral administration of the compounds is lowered. They are also suitable for prophylaxis and for the control of the sequelae of cerebral infarcts (apoplexia cerebri) such as stroke and cerebral ischaemias, and also for the treatment of extrapyramidal motor side effects of neuroleptics and of Parkinson's disease.

The compounds of the formula I and their physiologically acceptable acid addition salts can therefore be used as pharmaceutical active substances, in particular for anxiolytics, antidepressants, antipsychotics, neuroleptics and/or antihypertensives and also as intermediates for the production of other pharmaceutical active compounds.

The invention thus relates to the medicaments of the formula I and to their physiologically acceptable acid addition salts.

The invention also relates to pharmaceutical preparations, characterized in that they contain at least one compound of the formula I and/or one of its physiologically acceptable acid addition salts.

The invention relates in particular to pharmaceutical preparations comprising at least one compound selected from the group consisting of
a) 3-[4-(4-(4-cyanophenyl)-1-piperazinyl)butyl]-5-cyanoindole;
b) 3-[3-(4-(4-cyanophenyl)-1-piperazinyl)propyl]-5-cyanoindole;
c) 3-[4-(4-(4-fluorophenyl)-1-piperazinyl)butyl]-5-cyanoindole, methanesulfonate;
d) 3-[4-(4-(2-cyanophenyl)-1-piperazinyl)butyl]-5-cyanoindole;
e) 3-[4-(4-(3-fluoro-4-cyanophenyl)-1-piperazinyl)butyl]-5-cyanoindole.
f) 3-[4-(4-(4-fluorophenyl)-1-piperazinyl)butyl]-5-cyanoindole-hydrochloride.

The invention also relates to the medicaments of the formula I and to their physiologically acceptable acid addition salts as 5-hydroxytryptamine agonists and antagonists.

The radical Ar is a phenyl radical which is mono- or disubstituted by CN and/or F.

The radical Q is —$(CH_2)_3$— or —$(CH_2)_4$—.

The invention relates in particular to the compounds:
a) 3-[4-(4-(4-cyanophenyl)-1-piperazinyl)butyl]-5-cyanoindole;
b) 3-[3-(4-(4-cyanophenyl)-1-piperazinyl)propyl]-5-cyanoindole;
c) 3-[4-(4-(2-cyanophenyl)-1-piperazinyl)butyl]-5-cyanoindole;
d) 3-[4-(4-(3-fluoro-4-cyanophenyl)-1-piperazinyl)butyl]-5-cyanoindole and to the acid addition salts of the compounds mentioned.

A preferable object of the invention is 3-[4-(4-(4-fluorophenyl)-1-piperazinyl)butyl]-5-cyanoindole-hydrochloride.

The invention further relates to a process for the preparation of compounds of the formula I according to claim 1, and to their salts, characterized in that a compound of the formula II

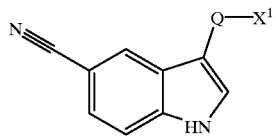

in which
- $X^1$ is X or $NH_2$ and
- X is Cl, Br, I, OH or a reactive functionally modified OH group, and
- Q has the meaning indicated, is reacted with a compound of the formula III

in which
- $X^2$ and $X^3$ can be identical or different and, if $X^1$=$NH_2$, are each X, or if $X^1$ is X, then $X^2$ and $X^3$ together are NH to form a cyclic compound, Ar has the meaning indicated,
or in that a compound of the formula IV

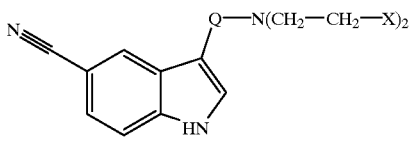

in which
X and Q have the meanings indicated, is reacted with a compound of the formula V

      Ar—NH$_2$      V in which
Ar has the meaning indicated,
or in that a base of the formula I which is obtained is converted into one of its acid addition salts by treating with an acid.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; but in particular in DE 4101686), namely under reaction conditions which are known and suitable for the reactions mentioned. In this case, use can also be made of variants which are known per se, but not mentioned here in greater detail.

If desired, the starting substances can also be formed in situ in such a way that they are not isolated from the reaction mixture, but immediately reacted further to give the compounds of the formula I. The compounds of the formula I can preferably be obtained by reacting compounds of the formula II with compounds of the formula III.

In the compounds of the formula II, $X^1$ is preferably X; accordingly in the compounds of the formula III $X^2$ and $X^3$ are preferably together NH. The radical X is preferably Cl or :Br; however, it can also be I, OH or a reactive modified OH group such as alkylsulfonyloxy having 1–6 C atoms (preferably methylsulfonyloxy) or arylsulfonyloxy having 6–10 C atoms (preferably phenyl- or p-tolylsulfonyloxy).

Accordingly, the compounds of the formula I are obtainable in particular by reaction of compounds of the formula II, in which $X^1$ is Cl or Br, with piperazine derivatives of the formula III, in which $X^2$ and $X^3$ together are an NH group (designated below as IIIa).

The compounds of the formulae II and in particular III are known in some cases; the unknown compounds of the formulae II and III can easily be prepared analogously to the known compounds.

Compounds of the formula II in which $X^1$ is OH are obtainable, for example, by reduction of the corresponding carboxylic acids or their esters. Treating with thionyl chloride, hydrogen bromide, phosphorus trichloride or similar halogen compounds gives the corresponding compounds of the formula II in which $X^1$ is Cl or Br. The corresponding sulfonyloxy compounds are obtainable from the compounds of the formula II in which $X^1$ is OH by reaction with the corresponding sulfonyl chlorides.

The iodine compounds of the formula II are obtainable, for example, by the action of potassium iodide on the associated p-toluenesulfonic acid esters. The compounds of the formula II in which $X^1$ is NH$_2$ can be prepared, for example, from the halides using potassium phthalimide.

The piperazine derivatives IIIa are in the main known and obtainable, for example, by reaction of di(2-chloroethyl)amine with the corresponding derivative of the aniline substituted on the phenyl ring. Compounds of the formula III ($X^2$ and $X^3$ each=X) can be prepared, for example, by reduction of diesters of the formula alkylOOC—CH$_2$—NAr—CH$_2$—COOalkyl to compounds of the formula HO—CH$_2$—CH$_2$—NAr—CH$_2$—CH$_2$—OH (III, $X^2$=$X^3$=OH) and, if appropriate, subsequent reaction with SOCl$_2$ or PBr$_3$.

The reaction of the compounds II and III proceeds according to methods such as are known from the literature for the alkylation of amines. The components can be fused with one another without a solvent being present, optionally in a closed tube or in an autoclave. However, it is also possible to react the compounds in the presence of a solvent inert to the reaction. Suitable solvents are, for example, hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, and optionally also mixtures of these solvents with one another or mixtures with water. The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylaniline, pyridine or quinoline or of an excess of the amine component of the formula II or of the piperazine derivative of the formula IIIa can be favorable. Depending on the conditions used, the reaction is generally from a few minutes to about 14 days, and the reaction temperature is preferably from approximately 0° C. to 150° C., more particularly from 20° C. to 130° C.

It is further possible to obtain a compound of the formula I by reacting a compound of the formula IV with a compound of the formula V. The compounds of the formulae IV and in particular V are known in some cases; the unknown compounds can easily be prepared in analogy to the known compounds. Thus compounds of the formula IV can easily be prepared by reaction of compounds of the formula II, in which $X^1$ is NH$_2$, with 1,2-dihaloethane, halogen preferably being chlorine or bromine. It is also possible to obtain compounds of the type IV by reaction of compounds of the formula II, in which $X^1$ is Cl, Br or I, with secondary amines of the formula HN(CH$_2$—CH$_2$—X)$_2$.

The primary amines of the formula V can be prepared starting from aniline by the various possibilities of electrophilic substitution on the Ar group which are known per se. It is further possible to convert appropriately substituted nitro compounds into the amines of the formula V by reduction.

The reaction of the compounds IV and V proceeds according to methods such as are known from the literature for the alkylation of amines. The components can be fused with one another without a solvent being present, optionally in a closed tube or in an autoclave, at normal pressure or at elevated pressure, an inert gas such as, for example, N$_2$ being added to increase the pressure. However, it is also possible to react the compounds in the presence of a solvent inert to the reaction. Suitable solvents are those previously mentioned for the reaction of II with III. The addition of an acid-binding agent to the reaction mixture can also have a favorable effect. The same bases as were previously described for the reaction of the compound II and III are suitable.

The optimum reaction time, depending on the reaction conditions selected, is generally from a few minutes to 14 days, and the reaction temperature is preferably from approximately 0° C. to 150° C., customarily from 20° C. to 130° C.

A base of the formula I can be converted with an acid into the associated acid addition salt, for example by reaction of equivalent amounts of the base and of the acid in an inert solvent such as ethanol and subsequent evaporation. For this reaction, suitable acids are particularly those which give physiologically acceptable salts. Inorganic acids can thus be used, e.g. sulfuric acid, nitric acid, hydrohalic acids such as hydrochloric acid or hydrobromic acid, phosphoric acids such as orthophosphoric acid, sulfamic acid, and further organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g. picrates, can be used for the isolation and/or purification of the compounds of the formula I.

The invention furthermore relates to the use of the compounds of the formula I and/or their physiologically acceptable salts for the production of pharmaceutical preparations, in particular by a non-chemical route. In this context, they can be brought into a suitable dose form together with at least one solid, liquid and/or semi-liquid excipient or auxiliary and if appropriate in combination with one or more further active compounds.

These preparations can be used as medicaments in human or veterinary medicine. Suitable excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc or petroleum jelly. In particular, tablets, pills, coated tablets, capsules, powders, granules, syrups, juices or drops are used for oral administration, suppositories for rectal administration, solutions, preferably oily or aqueous solutions, and further suspensions, emulsions or implants for parenteral administration, and ointments, creams or powders for topical application. The novel compounds can also be lyophilized and the lyophilisates obtained used, for example, for the production of injection preparations. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or one or more further active compounds, e.g., one or more vitamins.

The compounds of the formula I and their physiologically acceptable salts can be used in the therapeutic treatment of the human or animal body and in the control of illnesses. They are suitable for the treatment of disorders of the central nervous system such as states of tension, depressions and/or psychoses and of side effects in the treatment of hypertension (e.g. with α-methyldopa). The compounds can further be used in endocrinology and gynaecology, e.g. for the therapy of acromegaly, hypogonadism, secondary amenorrhoea, premenstrual syndrome, undesired puerperal lactation, and furthermore for the prophylaxis and therapy of cerebral disorders (e.g. migraine), in particular in geriatrics, similarly to certain ergot alkaloids and for the control of the sequelae of cerebral infarcts (apoplexia cerebri), such as stroke and cerebral ischaemias.

In this context, the substances according to the invention are generally administered in analogy to known, commercially available preparations (e.g. bromocriptine, dihydroergocornine), preferably in doses from approximately 0.2 to 500 mg, in particular from 0.2 to 50 mg, per dose unit. The daily dose is preferably from approximately 0.001 to 10 mg/kg of body weight. The low doses (approximately 0.2 to 1 mg per dose unit; approximately 0.001 to 0.005 mg/kg of body weight) are in this context particularly suitable for use as anti-migraine agents; for the other indications doses of from about 10 to 50 mg per dose unit are preferred. The specific dose for each patient depends, however, on all sorts of factors, for example on the activity of the specific compound employed, on the age, body weight, general state of health and sex, on the diet, on the time and route of administration, and on the excretion rate, pharmaceutical substance combination and severity of the particular disorder to which the therapy applies. Oral administration is preferred.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding The entire disclosure of all applications, patents and publications, cited above and below, and of corresponding German application No. 195 12 639.4, filed Apr. 5, 1995 is hereby incorporated by reference.

Above and below, all temperatures are indicated in ° C. In the following examples, "customary working up" means: water is added, if necessary, the mixture is adjusted, if necessary, depending on the constitution of the final product, to a pH of from 2 to 10 and extracted with ethyl acetate or dichloromethane, and the organic phase is separated off, dried over sodium sulfate, evaporated and purified by chromatography on silica gel and/or by crystallization.

EXAMPLE 1

A solution of 2.6 g of 3-(4-chlorobutyl)-5-cyanoindole ("A") and 1.7 g of 1-(4-cyanophenyl)piperazine ("B") in 200 ml of acetonitrile is stirred at 20° for 12 hours and worked up in the customary manner, and 3-[4-(4-(4-cyanophenyl)-1-piperazinyl)butyl]-5-cyanoindole, hydrochloride, m.p. 262.5–263.5°, is obtained.

The following are obtained analogously by reaction
of "A" with 1-(4-fluorophenyl)piperazine 3-[4-(4-(4-fluorophenyl)piperazinyl)butyl]-5-cyanoindole, hydrochloride, m.p. 248–249°;
of 3-(3-chloropropyl)-5-cyanoindole with "B" 3-[3-(4-(4-cyanophenyl)-1-piperazinyl)propyl]-5-cyanoindole, m.p. 219–220°;
of "A" with 1-(2-cyanophenyl)piperazine 3-[4-(4-(2-cyanophenyl)-1-piperazinyl)butyl]-5-cyanoindole, hydrochloride, m.p. 232°.

EXAMPLE 2

A solution of 10.8 g of 3-[4-N,N-bis(2-chloroethyl) aminobutyl)-5-cyanoindole and one equivalent of 3-fluoro-4-cyanoaniline in 200 ml of acetonitrile is stirred at room temperature for 12 hours and worked up in the customary manner, and 3-[4-(4-(3-fluoro-4-cyanophenyl)-1-piperazinyl)butyl]-5-cyanoindole, m.p. 117.5–118.5°, is obtained.

The following examples relate to pharmaceutical preparations:

Example A
Injection Vials

A solution of 100 g of an active compound of the formula I and 5 g of disodium hydrogen phosphate is adjusted to pH 6.5 in 3 l of double-distilled water using 2 N hydrochloric acid, sterile filtered, filled into injection vials and lyophilized under sterile conditions, and the vials are aseptically sealed. Each injection vial contains 5 mg of active compound.

Example B
Suppositories

A mixture of 20 g of an active compound of the formula I is fused with 100 g of soya lecithin and 1400 g of cocoa butter, poured into molds and allowed to cool. Each suppository contains 20 mg of active compound.

Example C
Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. The pH is adjusted to 6.8, and the solution is made up to 1 l and sterilized by irradiation. This solution can be used in the form of eye drops.

Example D
Ointment 500 mg of an active compound of the formula I are mixed with 99.5 g of petroleum jelly under aseptic conditions.

Example E
Tablets

A mixture of 1 kg of active compound of the formula I, 4 kg of lactose, 1.2 kg of potato starch, 0.2 kg of talc and 0.1 kg of magnesium stearate is compressed in a customary manner to give tablets in such a way that each tablet contains 10 mg of active compound.

Example F
Coated Tablets

Analogously to Example E, tablets are pressed which are then coated in a customary manner with a coating of sucrose, potato starch, talc, tragacanth and colorant.

Example G
Capsules 2 kg of active compound of the formula I are filled in a customary manner into hard gelatin capsules such that each capsule contains 20 mg of the active compound.

Example H
Ampoules

A solution of 1 kg of active compound of the formula I in 60 l of double-distilled water is sterile filtered, filled into ampoules and lyophilized under sterile conditions, and the ampoules are aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. The compound 3-[4-(4-(4-cyanophenyl)-1-piperazinyl)butyl]-5-cyanoindole hydrochloride.

2. A pharmaceutical composition comprising the compound of claim 1.

3. A process for the production of a pharmaceutical composition, comprising bringing the compound of claim 1 into a suitable dose form together with at least one solid, liquid or semi-liquid excipient or auxiliary.

4. A method comprising administering to a patient an anxiolytic, antidepressant, antipsychotic, neuroleptic or antihypertensive active effective amount of the compound of claim 1 for the treatment or control of an illness associated with such activity.

5. The method of claim 4, wherein the illness is a cerebral infarct.

6. The method of claim 4, wherein the illness is stroke or cerebral ischaemia.

7. The method of claim 4, wherein the illness is Parkinson's disease.

8. The method of claim 4, wherein the compound is administered in a daily dose amount of from approximately 0.001 to 10 mg/kg of body weight.

9. A method for treatment or control of depression which comprises administering to a patient an anti-depressant effective amount of the compound of claim 1.

10. The compound 3-[4-(4-(4-fluorophenyl)-1-piperazinyl)butyl]-5-cyanoindole hydrochloride.

11. A pharmaceutical composition comprising the compound of claim 10.

12. A process for the production of a pharmaceutical composition, comprising bringing the compound of claim 10 into a suitable dose form together with at least one solid, liquid or semi-liquid excipient or auxiliary.

13. A method comprising administering to a patient an anxiolytic, antidepressant, antipsychotic, neuroleptic or antihypertensive active effective amount of the compound of claim 10 for the treatment or control of an illness associated with such activity.

14. The method of claim 13, wherein the illness is a cerebral infarct.

15. The method of claim 13, wherein the illness is stroke or cerebral ischaemia.

16. The method of claim 13, wherein the illness is Parkinson's disease.

17. The method of claim 13, wherein the compound is administered in a daily dose amount of from approximately 0.001 to 10 mg/kg of body weight.

* * * * *